US008605963B2

(12) United States Patent
Gering et al.

(10) Patent No.: US 8,605,963 B2
(45) Date of Patent: Dec. 10, 2013

(54) ATLAS-BASED IMAGE COMPRESSION

(75) Inventors: David Thomas Gering, Waukesha, WI (US); Gopal Biligeri Avinash, Menomonee Falls, WI (US)

(73) Assignee: General Electric Company, Schenectady, NY (US)

( * ) Notice: Subject to any disclaimer, the term of this patent is extended or adjusted under 35 U.S.C. 154(b) by 1306 days.

(21) Appl. No.: 11/725,351

(22) Filed: Mar. 19, 2007

(65) Prior Publication Data

US 2008/0232700 A1     Sep. 25, 2008

(51) Int. Cl.
*G06K 9/00*     (2006.01)
*G06K 9/46*     (2006.01)

(52) U.S. Cl.
USPC ........... 382/128; 382/209; 382/232; 382/239; 382/241; 382/243

(58) Field of Classification Search
USPC .................. 382/128, 209, 232, 239, 241, 243
See application file for complete search history.

(56) References Cited

U.S. PATENT DOCUMENTS

| | | | |
|---|---|---|---|
| 5,014,334 A * | 5/1991 | Fukuhara et al. | 382/233 |
| 5,490,221 A | 2/1996 | Ransford et al. | |
| 5,502,778 A | 3/1996 | Ishikawa et al. | |
| 6,144,772 A * | 11/2000 | Garland et al. | 382/239 |
| 6,633,674 B1 | 10/2003 | Barnes et al. | |
| 6,891,973 B1 * | 5/2005 | Atsumi et al. | 382/232 |
| 6,912,319 B1 | 6/2005 | Barnes et al. | |
| 7,310,435 B2 * | 12/2007 | Mallya et al. | 382/128 |
| 2005/0100232 A1 * | 5/2005 | Sakanashi et al. | 382/238 |
| 2005/0259882 A1 * | 11/2005 | Dewaele | 382/243 |

FOREIGN PATENT DOCUMENTS

| | | |
|---|---|---|
| JP | 61184052 A | 8/1986 |
| JP | 8221557 A | 8/1996 |
| JP | 2005287927 A | 10/2005 |

OTHER PUBLICATIONS

Park et al. "Region-of-Interest Coding Based on Set Partitioning in Hierarchical Trees", IEEE Trans. on Circuits and Systems for Video Technology, v. 12, Feb. 2002, pp. 106-111.*
Baxes, Gregory. Digital Image Processing: principles and applications. New York: John Wiley & Sons, Inc, 1994. Print. p. 200.*
Krishnan, Karthik; "Efficient Transmission of Compressed Data for Remote Volume Visualization"; IEEE Transactions on Medical Imaging, vol. 25, No. 9, pp. 1189-1199; Sep. 2006.

* cited by examiner

*Primary Examiner* — Matthew Bella
*Assistant Examiner* — Julian Brooks
(74) *Attorney, Agent, or Firm* — Fletcher Yoder, P.C.

(57) ABSTRACT

A technique for selecting portions of a medical image data set to be stored and portions of the medical image data set to be discarded in order to reduce the overall amount of image data that is stored for each image data set. The selection is based on the clinical purpose for obtaining the medical image data. The clinical purpose for obtaining the medical image is used to select an atlas. The atlas is labeled with information that establishes the relative relevance of various regions of the atlas. The atlas is aligned to the image and the labeling information is transferred from the atlas to the medical image. Each region of the medical image is then processed based on the labeling information received from the atlas. The regions of greatest relevance are stored at their full resolution. Regions of lesser relevance are stored at less than the full resolution. Finally, regions of no relevance are discarded and not stored at all.

30 Claims, 5 Drawing Sheets

ATLAS-BASED IMAGE COMPRESSION

BACKGROUND

The invention relates generally to the field of medical image data storage. More particularly, the invention relates to a technique for reducing the amount of medical image data of a medical image data set that is stored in long-term storage.

Picture archiving and communications systems, or PACS, have become an extremely important component in the management of digitized image data, particularly in the field of medical imaging. Such systems often function as central repositories of image data, receiving the data from various sources, such as medical imaging systems. The image data is stored and made available to radiologists, diagnosing and referring physicians, and other specialists via network links. Improvements in PACS have led to dramatic advances in the volumes of image data available, and have facilitated loading and transferring of voluminous data files both within institutions and between the central storage location and remote clients.

In the medical diagnostics field, depending upon the imaging modality, digitized data may be acquired and processed for a substantial number of images in a single examination, each image representing a large data set defining discrete picture elements (pixels) of a reconstructed image, or volume elements (voxels) in three dimensional data sets. Computed tomography (CT) imaging systems, for example, can produce numerous separate images along an anatomy of interest in a very short examination timeframe. Other imaging modalities are similarly capable of producing large volumes of useful image data, including magnetic resonance imaging (MRI) systems, digital X-ray systems, X-ray tomosynthesis systems, ultrasound systems, positron emission tomography (PET) systems, and so forth. Ideally, all such images are stored centrally on the PACS, and made available to the radiologist for review and diagnosis.

Various techniques have been proposed and are currently in use for analyzing and compressing large data files, such as medical image data files. Image data files typically include streams of data descriptive of image characteristics, typically of intensities or other characteristics of individual pixels or voxels in the reconstructed image. In the medical diagnostic field, these image files are typically created during an image acquisition, encoding or processing (e.g., reconstruction) sequence, such as in an X-ray, MRI, CT, or other system, or in a processing station designed to process image data from such systems. The image data may be subsequently processed or reprocessed, such as to adjust dynamic ranges, or to enhance certain features shown in the image, for storage, transmittal and display.

While image files may be stored in raw and processed formats, many image files are quite large, and would occupy considerable disc or storage space. The almost exponential increases in the resolutions of imaging systems that has occurred and which appears will continue into the future is leading to the creation of ever larger image files, typically including more data as a result of the useful dynamic range of the imaging system, the size of the matrix of image pixels and voxels, and the number of images acquired per examination. In addition, the processing and memory requirements for current PACS systems for new clinical applications and techniques is beginning to tax current system capabilities, such as the ever increasing clinical needs for volumetric data sampled over time and for the use of multiple energy volumes for better visualization of anatomical and functional features.

In addition to occupying large segments of available memory, large image files can be difficult or time consuming to transmit from one location to another. In a typical medical imaging application, for example, a scanner or other imaging device will typically create raw data which may be at least partially processed at the scanner. The data is then transmitted to other image processing circuitry, typically including a programmed computer, where the image data is further processed and enhanced. Ultimately, the image data is stored either locally at the system, or in the PACS for later retrieval and analysis. In all of these data transmission steps, the large image data file must be accessed and transmitted from one device to another.

Current image handling techniques include compression of image data within the PACS environment to reduce the storage requirements and transmission times. Such compression techniques generally, however, compress entire files, including descriptive header information which could be useful in accessing or correlating images for review. Moreover, current techniques may not offer sufficiently rapid compression and decompression of image files to satisfy increasing demands on system throughput rates and access times. Finally, alternative compression and decompression techniques do not offer the desired compression ratios, in combination with rapid compression and decompression in a client-server environment.

Another drawback of existing compression techniques is the storage, access and transmission of large data files even when a user cannot or does not desire to view the reconstructed image in all available detail. For example, in medical imaging, extremely detailed images may be acquired and stored, while a radiologist or physician who desires to view the images may not have a view port capable of displaying the images in the resolution in which they are stored. Thus, transmission of the entire images to a remote viewing station, in relatively time consuming operations, may not provide any real benefit and may slow reading or other use of the images. Furthermore, only certain portions of a medical image may be relevant for diagnosis or treatment. Thus, considerable storage space in a PACS may be allocated to the storage of medical image data that is irrelevant for the patient's diagnosis and treatment. This problem becomes even more acute as imaging systems achieve greater and greater resolutions, which correspond to a need for even more data storage space.

There is a need, therefore, for an improved image data compression and decompression technique which provides rapid compression and decompression of image files, and which obtains improved compression ratios and transmission times. In addition, there also is a need for a technique which permits compressed image data files to be created and transmitted in various resolutions or sizes, depending upon the bandwidth and desired or available resolution on a client side. Furthermore, there is a particular need for a technique to enable image data storage systems to accommodate the increase in data required to store medical images obtained with ever increasing resolutions of imaging systems.

BRIEF DESCRIPTION

A technique is presented for selecting portions of a medical image data set to be stored and portions of the medical image data set to be discarded in order to reduce the overall amount of image data that is stored for each image data set. The selection is based on the clinical purpose for obtaining the medical image data. The clinical purpose for obtaining the medical image is used to select an atlas. The atlas is labeled with information that establishes the relative relevance of various regions of the atlas. The atlas is aligned to the image and the labeling information is transferred from the atlas to the medical image. Each region of the medical image is then processed based on the labeling information received from the atlas. The regions of greatest relevance are stored at their full resolution. Regions of lesser relevance are stored at less than the full resolution. Finally, regions of no relevance are discarded and not stored at all.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
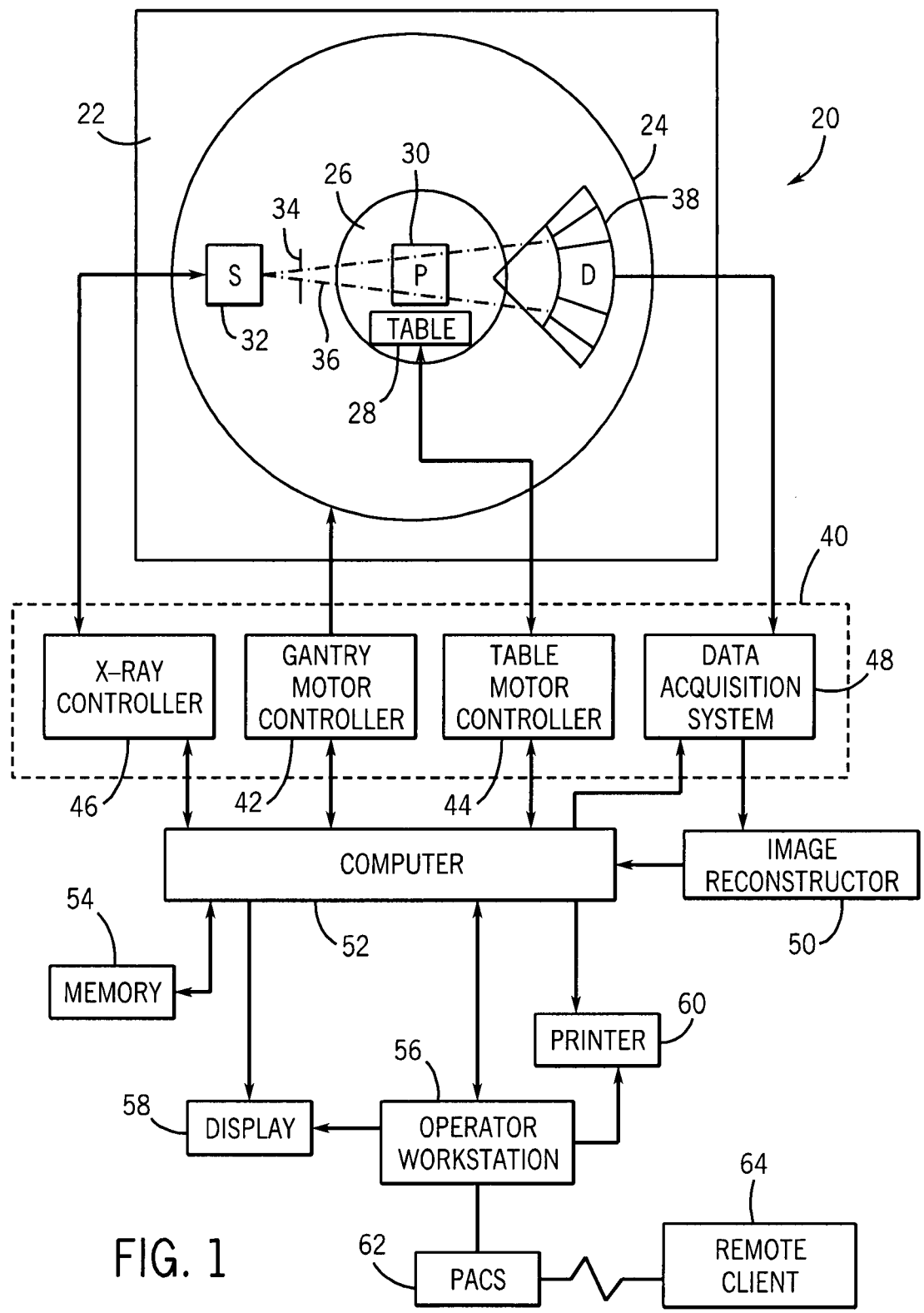
FIG. 1 is a schematic view of an exemplary imaging system, in this case a computed tomography ("CT") imaging system, designed to implement the enhanced image data storage scheme in accordance with an exemplary embodiment of the present technique.

Referring now to FIG. 1, the present invention will be described as it might be applied in conjunction with an exemplary imaging system, in this case a computed tomography (CT) imaging system. In general, however, it should be borne in mind that the present techniques may be used with image data produced by any suitable imaging modality. In a typical application, the imaging system may be designed both to acquire original image data and to process the image data for display and analysis is presented. As noted below, however, in certain applications the image data acquisition and subsequent processing (e.g., for the transformations and compression described below) may be carried out in physically separate systems or work stations. The illustrated embodiment of the CT imaging system 20 has a frame 22, a gantry 24, and an aperture (imaging volume or CT bore volume) 26. A patient table 28 is positioned in the aperture 26 of the frame 22 and the gantry 24. The patient table 28 is adapted so that a patient 30 may recline comfortably during the examination process.

The illustrated embodiment of the CT imaging system 20 has an X-ray source 32 positioned adjacent to a collimator 34 that defines the size and shape of the X-ray beam 36 that emerges from the X-ray source 32. In typical operation, the X-ray source 32 projects a stream of radiation (an X-ray beam) 36 towards a detector array 38 mounted on the opposite side of the gantry 24. All or part of the X-ray beam 36 passes through a subject, such as a patient 30, prior to impacting the detector array 38. It should be noted that all or part of the X-ray beam 36 may traverse a particular region of the patient 30, such as the liver, pancreas, heart, and so on, to allow a scan of the region to be acquired. The detector array 38 may be a single slice detector or a multi-slice detector and is generally formed by a plurality of detector elements. Each detector element produces an electrical signal that represents the intensity of the incident X-ray beam 36 at the detector element when the X-ray beam 36 strikes the detector array 38. These signals are acquired and processed to reconstruct an image of the features within the patient 30.

The gantry 24 may be rotated around the patient 30 so that a plurality of radiographic views may be collected along an imaging trajectory described by the motion of the X-ray source 32 relative to the patient 30. In particular, as the X-ray source 32 and the detector array 38 rotate along with the gantry 24, the detector array 38 collects photons resulting from X-ray beam attenuation at the various view angles relative to the patient 30 and produces signals or data representative of the incident photons. Data collected from the detector array 38 then undergoes pre-processing and filtering to condition the data to represent the line integrals of the attenuation coefficients of the scanned patient 30. The processed data, commonly called projections, are then filtered and back projected to formulate an image of the scanned area. Thus, an image or slice is acquired which may incorporate, in certain modes, less or more than 360 degrees of projection data, to formulate an image.

Rotation of the gantry 24 and operation of the X-ray source 32 are controlled by a system controller 40, which furnishes both power and control signals for CT examination sequences. Moreover, the detector array 38 is coupled to the system controller 40, which commands acquisition of the signals generated in the detector array 38. The system controller 40 may also execute various signal processing and filtration functions, such as for initial adjustment of dynamic ranges, interleaving of digital image data, and so forth. In general, system controller 40 commands operation of the imaging system 20 to execute examination protocols and to process acquired data. In the present context, system controller 40 also includes signal processing circuitry, typically based upon a general purpose or application-specific digital computer, associated memory circuitry for storing programs and routines executed by the computer, as well as configuration parameters and image data, interface circuits, and so forth. The system controller 40 includes a gantry motor controller 42 that controls the rotational speed and position of the gantry 24 and a table motor controller 44 that controls the linear displacement of the patient table 28 within the aperture 26. In this manner, the gantry motor controller 42 rotates the gantry 24, thereby rotating the X-ray source 32, collimator 34 and the detector array 38 one or multiple turns around the patient 30. Similarly, the table motor controller 44 displaces the patient table 28, and thus the patient 30, linearly within the aperture 26. Additionally, the X-ray source 32 may be controlled by an X-ray controller 46 disposed within the system controller 40. Particularly, the X-ray controller 46 may be configured to provide power and timing signals to the X-ray source 32.

In the illustrated embodiment, the system controller 40 also includes a data acquisition system 48. In this exemplary embodiment, the detector array 38 is coupled to the system controller 40, and more particularly to the data acquisition system 48. The data acquisition system 48 typically receives sampled analog signals from the detector array 38 and converts the data to digital signals for subsequent processing. An image reconstructor 50 coupled to the computer 52 may receive sampled and digitized data from the data acquisition system 48 and performs high-speed image reconstruction. Alternatively, reconstruction of the image may be done by the computer 52. Once reconstructed, the image produced by the imaging system 10 reveals internal features of the patient 30.

The data collected by the data acquisition system 48, or the reconstructed images, may be transmitted to the computer 52 and to a memory 54. It should be understood that any type of memory to store a large amount of data may be utilized by such an exemplary imaging system 10. Also the computer 52 may be configured to receive commands and scanning parameters from an operator via an operator workstation 56 typically equipped with a keyboard and other input devices. An operator may control the CT imaging system 20 via the operator workstation 56. Thus, the operator may observe the reconstructed image and other data relevant to the system from computer 52, initiate imaging, and so forth.

The CT imaging system 20 also has a display 58 that is coupled to the operator workstation 56 and the computer 52 and may be utilized by a user to observe the reconstructed image, as well as to provide an interface for control of the operation of the CT imaging system 20. In this embodiment, a printer 60 is present to enable a hard copy of a medical image to be printed. In the illustrated embodiment, the CT imaging system 20 is coupled to a picture archiving and communications system (PACS) 62 via the operator workstation 56 for long-term storage of image data. It should be noted that the PACS 62 may be coupled to a remote system 64, such as radiology department information system (RIS), hospital information system (HIS) or to an internal or external network, so that others at different locations may gain access to the image and to the image data. However, access to the image data may also be obtained remotely through the PACS 62.

It should be further noted that the computer 52 and operator workstation 56 may be coupled to other output devices, such as a standard or special purpose computer monitor and associated processing circuitry. One or more operator workstations 56 may be further linked in the CT imaging system 20 for outputting system parameters, requesting examinations, viewing images, and so forth. In general, displays, printers, workstations, and similar devices supplied within the CT imaging system 20 may be local to the data acquisition components, or may be remote from these components, such as elsewhere within an institution or hospital, or in an entirely different location, linked to the imaging system CT via one or more configurable networks, such as the Internet, virtual private networks, and so forth.

As noted above, it should be borne in mind that the CT system referred to herein is merely one exemplary source of image data that may be handled in accordance with the present techniques. Most such systems will include operator interfaces and software specifically adapted to acquire image data and to at least partially process the data in accordance with the specific physics of the imaging modality. Indeed, other arrangements of CT systems, other reconstruction techniques, and so forth may give rise to image data that may be managed as described herein.

Figure 2:
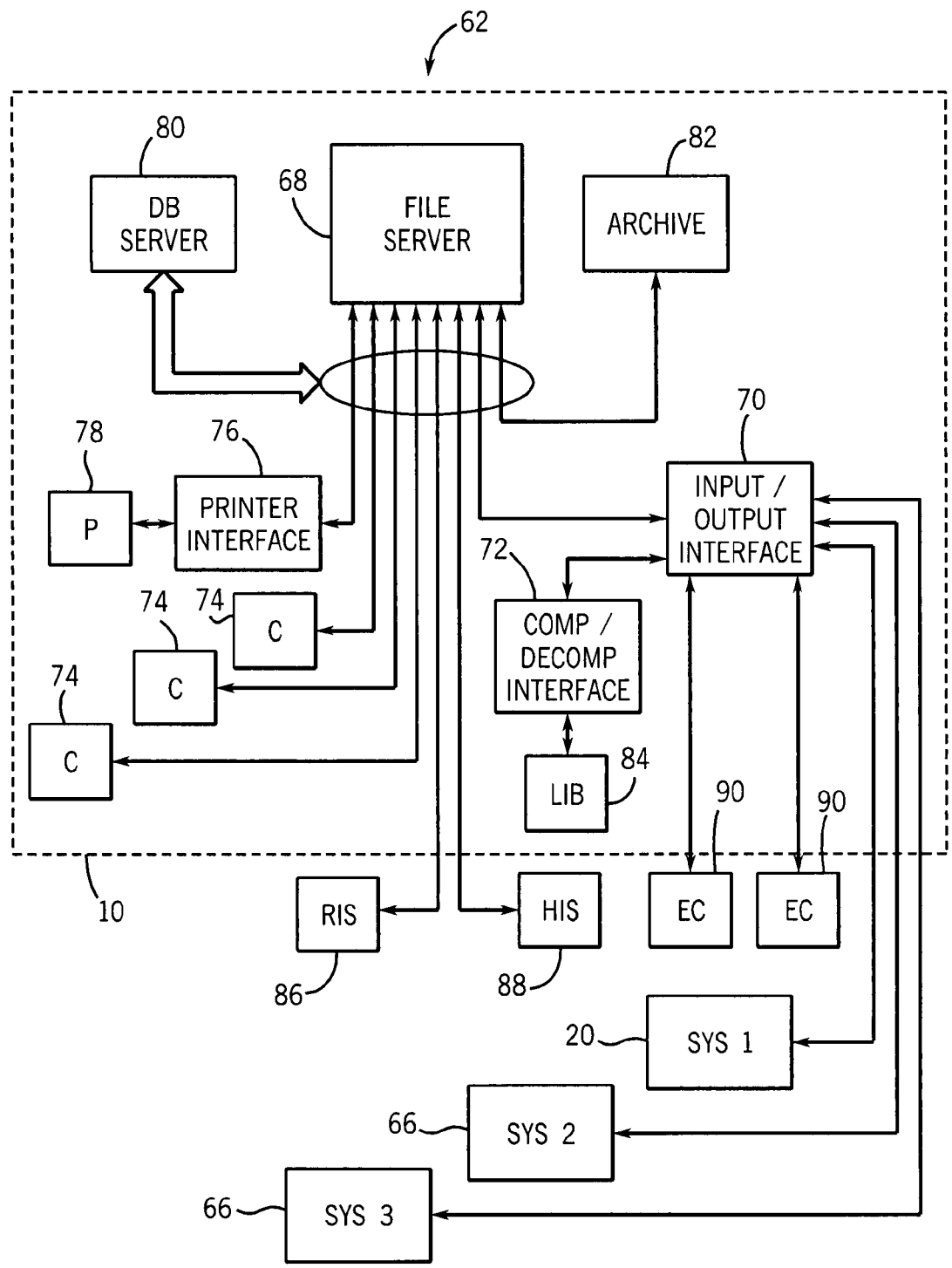
FIG. 2 is a diagrammatical representation of a picture archiving and communication system, or PACS, for receiving and storing image data from the imaging system of FIG. 1, in accordance with an exemplary embodiment of the present technique.

Referring generally to FIG. 2, an exemplary embodiment of a PACS 62 for receiving, compressing and decompressing image data is presented. In the illustrated embodiment, the CT imaging system 20 is used for short-term storage of image data only. Memory 54 of the CT imaging system 20 is limited and cannot be used to store image data with any degree of permanence, particularly when the system is used to carry out examinations for a large number of patients in a clinic, hospital or other institution. For example, data space occupied by old image data may be written over by new image data. The PACS 62 is used for long-term storage of medical image data. In the illustrated embodiment, PACS 62 receives image data from CT imaging system 20, as well as several other separate imaging systems designated by reference numeral 66. As will be appreciated by those skilled in the art, the imaging systems may be of various type and modality, such as MRI systems, PET systems, radio fluoroscopy (RF), computed radiography (CR), ultrasound systems, digital X-ray systems, X-ray tomosynthesis systems, ultrasound systems, and so forth. Moreover, the systems may include processing stations or digitizing stations, such as equipment designed to provide digitized image data based upon existing film or hard copy images. It should also be noted that the systems supplying the image data to the PACS may be located locally with respect to the PACS, such as in the same institution or facility, or may be entirely remote from the PACS, such as in an outlying clinic or affiliated institution. In the latter case, the image data may be transmitted via any suitable network link, including open networks, proprietary networks, virtual private networks, and so forth.

PACS 62 includes one or more file servers 68 designed to receive and process image data, and to make the image data available for decompression and review. File server 68 receives the image data through an input/output interface 70. Image data may be compressed in routines accessed through a compression/decompression interface 72. As described more fully below, compression/decompression interface 72 serves to compress the incoming image data rapidly and optimally, while maintaining descriptive image data available for reference by file server 68 and other components of the PACS. Where desired, compression/decompression interface 72 may also serve to decompress image data accessed through the file server 68. The file server 68 is also coupled to internal clients, as indicated at reference numeral 74, each client typically including a work station at which a radiologist, physician, or clinician may access image data from the server, decompress the image data, and view or output the image data as desired. Clients 74 may also input information, such as dictation of a radiologist following review of examination sequences. Similarly, file server 68 may be coupled to one or more interfaces, such as a printer interface 76 designed to access and decompress image data, and to output hard copy images via a printer 78 or other peripheral.

A database server 80 is used to associate image data, and other work flow information within the PACS, by reference to one or more file servers 68. In the presently contemplated embodiment, database server 80 may include cross-referenced information regarding specific image sequences, referring or diagnosing physician information, patient information, background information, work list cross-references, and so forth. The information within database server 80 serves to facilitate storage and association of the image data files with one another, and to allow requesting clients to rapidly and accurately access image data files stored within the system.

Similarly, file server 68 is coupled to one or more archives 82, such as an optical storage system, which serve as repositories of large volumes of image data for backup and archiving purposes. Techniques for transferring image data between file server 68, and any memory associated with file server 68 forming a short-term storage system, and archive 82, may follow any suitable data management scheme, such as to archive image data following review and dictation by a radiologist, or after a sufficient time has lapsed since the receipt or review of the image files.

In the illustrated embodiment, other components of the PACS system or institution may be integrated with the foregoing components to further enhance the system functionality. For example, a compression/decompression library 84 is coupled to compression/decompression interface 72 and serves to store compression routines, algorithms, look up tables, and so forth, for access by input/output interface 70 (or other system components) upon execution of compression and decompression routines (i.e. to store various routines, software versions, code tables, and so forth). In practice, compression/decompression interface 72 may be part of compression/decompression library 84. Library 84 may also be coupled to other components of the system, such as internal clients 74 or printer interface 76, serving similarly as a library or store for the compression and decompression routines and algorithms. Although illustrated as a separate component, it should be understood that compression/decompression library 84 may be included in any suitable server or memory device, including within file server 68. Moreover, code defining the compression and decompression processes described below may be loaded directly into compression/decompression interface 72 and/or compression/decompression library 84, or may be loaded or updated via network links, including wide area networks, open networks, and so forth.

Additional systems may be linked to the PACS, such as directly to server 80, or through interfaces such as input/output interface 70. In the embodiment illustrated in FIG. 2, a radiology department information system or RIS 86 is linked to file server 68 to facilitate exchanges of data, typically cross-referencing data within database server 80, and a central or departmental information system or database. Similarly, a hospital information system or HIS 88 may be coupled to database server 80 to similarly exchange database information, workflow information, and so forth. Where desired, such systems may be interfaced through data exchange software, or may be partially or fully integrated with the PACS system to provide access to data between the PACS database and radiology department or hospital databases, or to provide a single cross-referencing database. Similarly, external clients, as designated at reference numeral 90, may be interfaced with the PACS to enable images to be viewed at remote locations. Such external clients may employ decompression software, or may receive image files already decompressed by compression/decompression interface 72. Again, links to such external clients may be made through any suitable connection, such as wide area networks, virtual private networks, and so forth.

In the illustrated embodiment, the PACS 62 provides for multi-resolution (or multi-size) image data compression. Where a user does not desire to view a full image with maximum resolution, or where the user view port is limited, such multiresolution image compression facilitates transfer of a reduced size image to the user for viewing, with excellent image quality. Moreover, the multiresolution image compression may allow a user to view a reduced size or reduced resolution image relatively rapidly, and to "zoom" on the image thereafter by transfer of only a portion of the compressed data corresponding to components of the greater sized image not already transferred. The additional data is then processed and combined with the reduced size image data to obtain the larger sized image. In addition, the technique described below utilizes purpose-driven image data storage to reduce the amount of stored image data associated with an image stored in the PACS 62.

It should be noted that the processing and storage of the image data as described below may be performed in the PACS 62, or in any other suitable system component or components. The processing will typically be embodied in computer code that can be stored and executed on any one or more than one of the computers of the acquisition the PACS, an operator workstation, server, and so forth, so long as the system is capable of performing the computations involved.

The multi-resolution implementation may be based partially upon lossless integer wavelet decomposition. Specifically, as will be recognized by those skilled in the art, wavelet decomposition involves a dyadic filtering and sub-sampling process. This creates a hierarchical set of sub-bands. As will be discussed in more detail below, a wavelet transformed image data set includes low frequency components along with high frequency components, which may be considered as noise or variations from the low frequency components. A single level wavelet decomposition results in a decomposed data set which includes one low frequency sub-band LL, along with three high frequency ones LH, HL, and HH. Subsequent decomposition may be considered to produce a further data set in which the low frequency sub-band is further decomposed into a set of sub-bands, including a low frequency band, along with three additional high frequency sub-bands. The wavelet transformation technique may be carried out on two dimensional or three dimensional (or higher dimension) data sets.

Figure 3:
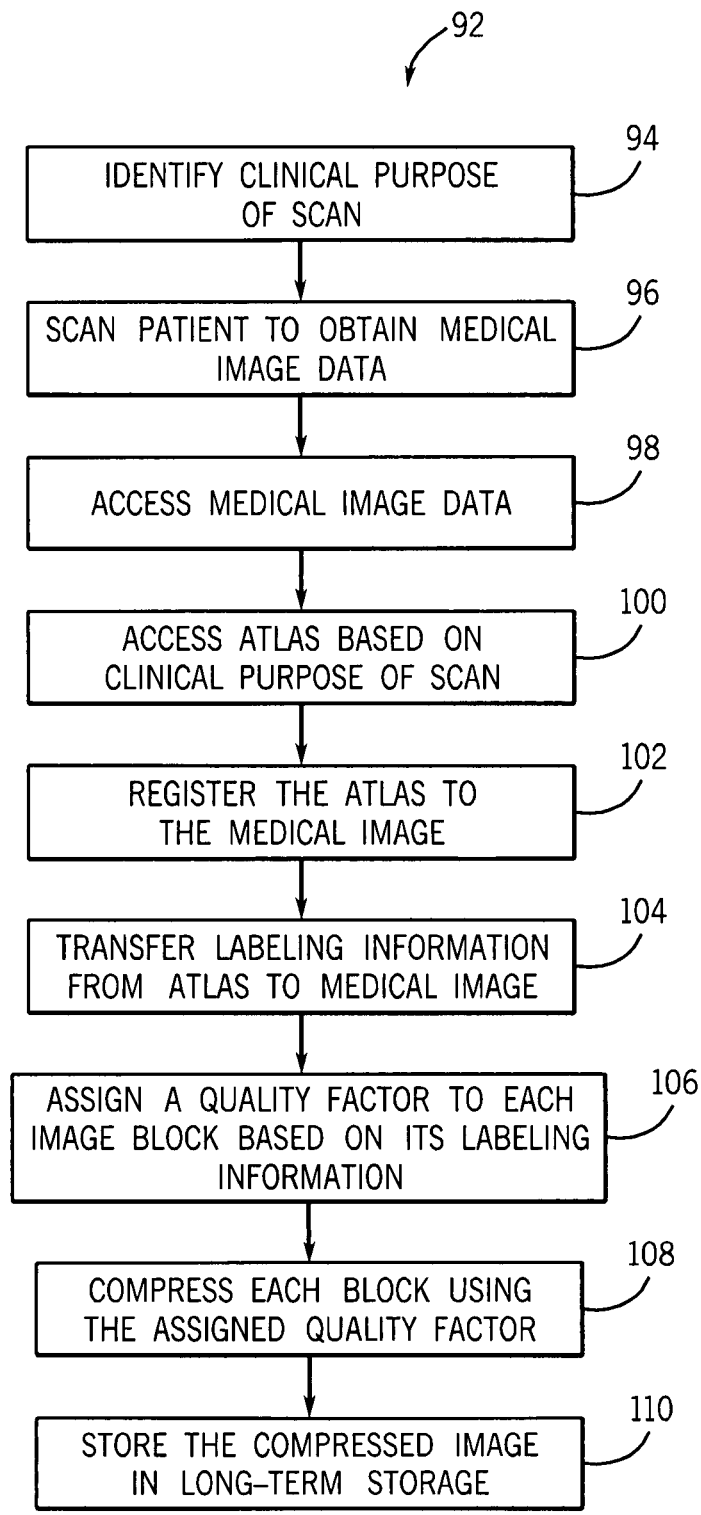
FIG. 3 is a block diagram of a technique for selectively storing medical image data based on an atlas, in accordance with an exemplary embodiment of the present invention.

Referring generally to FIG. 3, a technique is presented for selectively storing image data based on an atlas that serves as a reference for image data compression, represented generally by reference numeral 92. The technique enables the amount of medical image data that is stored in the PACS 62 for each medical image data set to be reduced. The regions of the image that are the most relevant, as defined by the clinical purpose for the scan, are stored in the PACS 94 with their full resolution. However, less relevant regions of the medical image data set are stored with a lower resolution, thereby requiring less data storage space. Still other regions of the medical image, which are irrelevant, are discarded and, thus, not stored in the PACS 62 at all, further reducing the amount of data storage space required to store the image data set. The image may be further decomposed into lower resolution levels.

As will be discussed in more detail below, an anatomical atlas is used to assign each region of the image with a quality factor. The quality factor establishes the amount of data compression that a particular region experiences before the region is stored. In this embodiment, a quality factor of one hundred would result in the image data being compressed with lossless compression, and, therefore, with full resolution. Medical image data with a quality factor of zero would not be compressed, or stored. Instead this medical image data would be discarded from the PACS. Medical image data with a quality factor between one hundred and zero would be compressed with lossy compression at less than full resolution. This technique may be performed by the CT imaging system 20 and the PACS 62 described above.

The technique calls for identifying the clinical purpose for obtaining the medical image data, as represented generally by block 94. The clinical purpose of the scan may be for any of a myriad of clinical purposes, such as an angiogram, a mammogram, a perfusion, to locate a tumor, an aneurysm, blocked blood vessels, etc, performed in any of the various portions of the body. This enables a user to establish what portion of the body to scan. In addition, the clinical purpose for obtaining the image data establishes the relative importance of the anatomical features or regions that will be in the medical image data set and, therefore, the atlas to use.

An imaging system, such as the CT imaging system 20, is used to scan the patient to obtain the desired medical image data, represented generally by block 96. In this embodiment, the CT imaging system 20 is not used for long-term storage of medical image data. Instead, long-term storage of medical image data occurs in the PACS 62. However, in other embodiments of the present technique, an imaging system may be used for long-term storage of medical image data. The medical image data that is obtained from scanning the patient is obtained at a single resolution, typically the highest, or greatest, resolution available from the CT imaging system 20. As noted above, this technique is applicable for use with imaging systems other than the CT imaging system 20.

The full resolution medical image data obtained by the imaging system is accessed for processing for long-term storage, represented generally by block 98. In the illustrated embodiment, the medical image data is accessed at the CT imaging system 20 by an operator at the operator workstation 56.

A user selects an atlas from among a plurality of atlases based on the clinical purpose of the scan, as represented by block 100. The plurality of atlases may be stored in the CT imaging system 20 or in the PACS 62. In the illustrated embodiment, an operator at the operator workstation 56 of the CT imaging system 20 selects the atlas from a menu of atlases. The atlas is then retrieved from memory either from the CT imaging system 20 or the PACS 62. Alternatively, a system operator may select the purpose for obtaining the image data from a menu or list or purposes, thereby directing the system to automatically identify an appropriate atlas and execute the steps of the technique. In the illustrated embodiment, the atlas comprises image data of at least three-dimensions of image data.

Each of the atlases is labeled with information that may be transferred to the medical image. In this embodiment, the labeling information includes the quality factors for various anatomical features in the atlas. The anatomical feature, or features, that are the subject of the scan determines the atlas that is used. Depending on the clinical purpose of the scan, an anatomical feature may be of great interest in one medical image and of little or no interest in another medical image. For example, if the purpose of the scan is to enable a radiologist to look for tumors in the brain, brain tissues would be the most relevant anatomical features and other anatomical features, such as bone, would be of lesser relevance. Therefore, in this example, an atlas could be selected that corresponds to a scan for brain tissue. In this example, the brain tissues in this atlas would be labeled with a quality factor of one hundred, while other anatomical features, such as bone, could be labeled with lower quality factors. However, if the purpose for the scan is to locate possible skull fractures, an atlas could be selected that corresponds to a scan of the skull. In this example, the skull in this atlas would be labeled with quality factors of one hundred, while other anatomical features, such as the brain, could be labeled with lower quality factors. In addition, an atlas may be comprised of two dimensional or three-dimensional image data.

The atlas is registered with the image data to align the anatomical features in the atlas with their corresponding anatomical features in the medical image data, represented generally by block 102. The size and shape of the anatomical features in the medical image data may differ from those in the atlas. Therefore, the atlas is deformed so that the anatomical features in the atlas are aligned with their corresponding anatomical features in the medical image. In some instances alignment of the atlas to the image is not required. For example, when the image data is acquired using an atlas.

Once aligned, the labeling information in the atlas is transferred to the medical image data, as represented generally by block 104. The registration is performed by a registration algorithm. The algorithm may be stored on the CT imaging system 20 or the PACS 62. In the illustrated embodiment, an operator at the operator workstation 56 initiates the execution of the registration algorithm.

After registration, quality factors are assigned to each image block, or region, of a medical image, represented generally by block 106. The image blocks contain the medical image data and may be individual voxels or groups of voxels that represent anatomical features or regions of the medical image.

Each image block is then compressed based on the assigned quality factor, as represented generally by block 108. Based on its quality factor, each image block may be compressed with lossless compression, lossy compression, or simply discarded. The data compression is performed by a compression algorithm. The data compression may include multi-resolution decomposition of the image data. In the illustrated embodiment, the data compression is performed in the PACS 62. In addition, prior to compression the labeled medical image data may be decomposed using wavelet decomposition into a plurality of resolution levels.

The compressed image data is then stored in long-term storage, such as in the PACS 62, represented generally by block 110. The medical image data may then be retrieved and decompressed at later times for viewing by a radiologist or other medical personnel.

Figure 4:
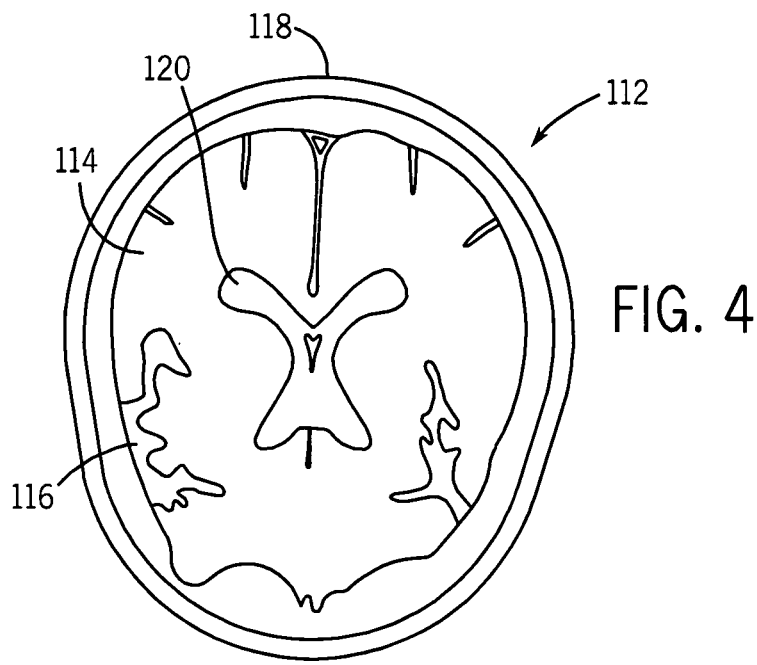
FIG. 4 is a representation of a medical image slice of a patient's brain, in accordance with an exemplary embodiment of the present invention.

Referring generally to FIG. 4, a medical image slice of a patient's brain taken along the transverse plane is presented, represented generally by reference numeral 112. The brain image slice 112 comprises white matter 114 and gray matter 116. The skull 118 surrounds and protects the white matter 114 and gray matter 116. Within the brain are spaces that hold cerebrospinal fluid 120. For brevity, other anatomical features that are present in the brain are not discussed.

Figure 5:
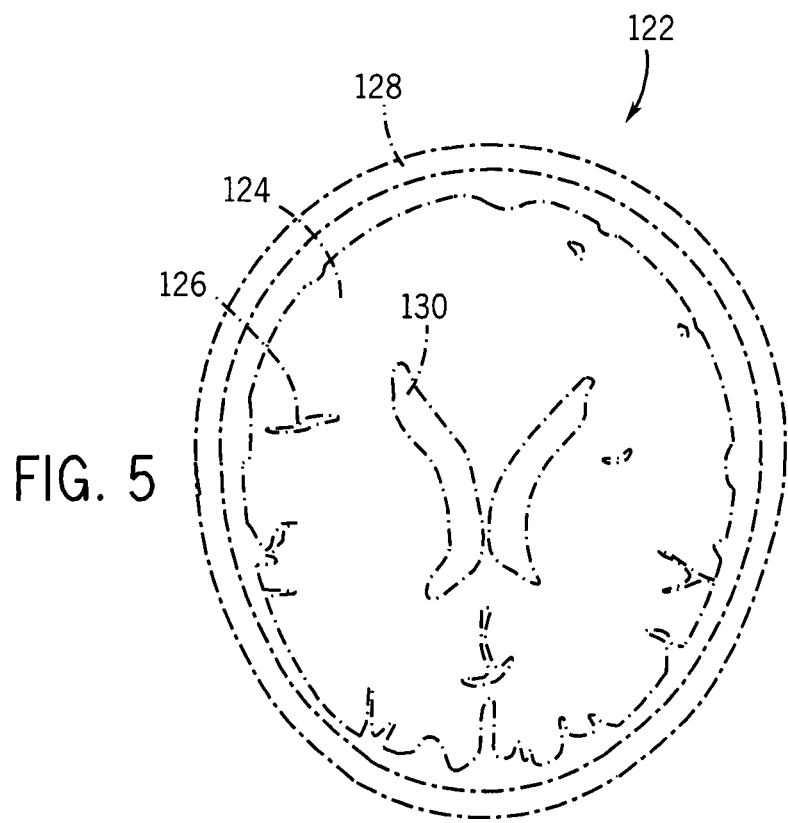
FIG. 5 is a representation of a medical image slice of an atlas of a brain, in accordance with an exemplary embodiment of the present invention.

Referring generally to FIG. 5, an atlas of the brain is presented, represented generally by reference numeral 122. The atlas 122 also contains regions corresponding to white matter 124, gray matter 126, a skull 128, and cerebrospinal fluid 130. The image blocks of the atlas 122 are labeled with quality factors. In this embodiment, the atlas was selected based on the clinical purpose of examining brain tissue. The image blocks corresponding to the white matter 124 and gray matter 126 are each labeled with a quality factor to indicate that they are the most relevant tissues. The image blocks that comprise the skull 128 are labeled with a quality factor to indicate that the skull is less relevant than the brain tissue. Finally, the image blocks corresponding to the cerebrospinal fluid 130 are labeled with quality factor to indicate that they are irrelevant.

Figure 6:
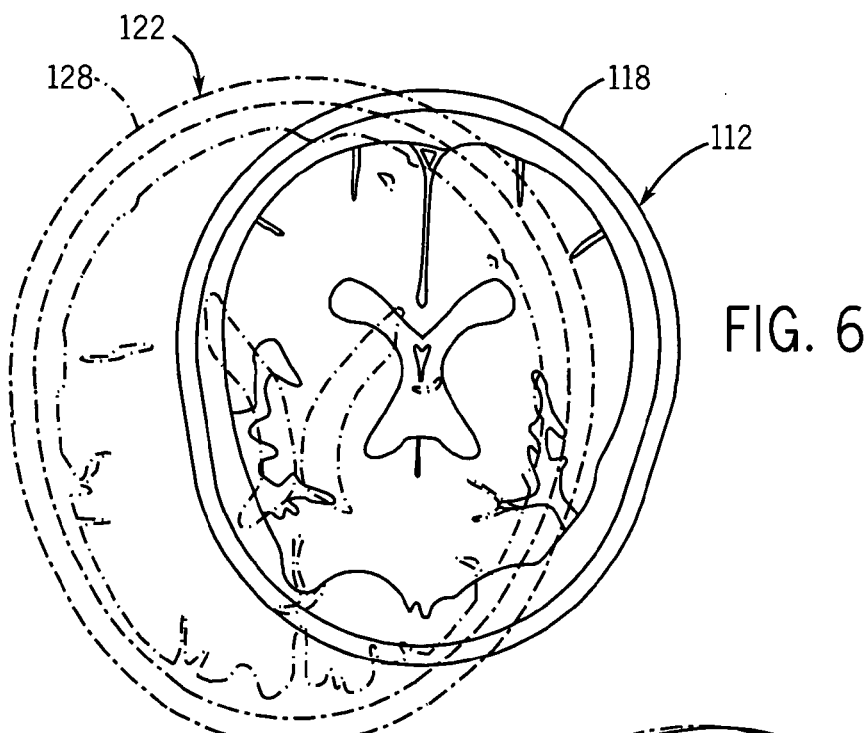
FIG. 6 is a representation of an initial alignment of the patient's brain of FIG. 4 with the atlas of a brain of FIG. 5, in accordance with an exemplary embodiment of the present invention.
Figure 7:
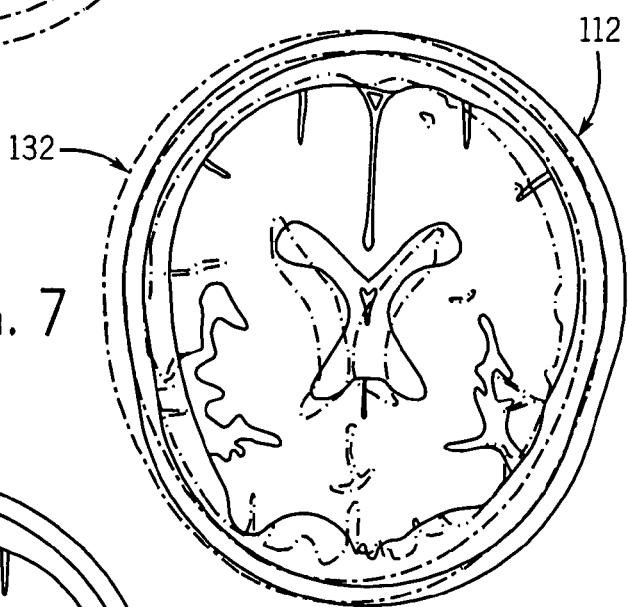
FIG. 7 is a representation of the final alignment of the patient's brain of FIG. 4 with the atlas of a brain of FIG. 5, in accordance with an exemplary embodiment of the present invention.

Referring generally to FIGS. 6 and 7, the brain image slice 112 and the atlas 122 are shown being brought into alignment. In FIG. 6, the brain image slice 112 and the atlas 122 are shown being overlaid prior to alignment. In FIG. 7, the atlas 132 has been deformed to bring it into alignment with the brain image slice 112. The quality factors are then transferred to the medical image data in the brain image slice 112. Once labeled, the medical image data may be compressed based on the quality factors and stored in long-term data storage.

Figure 8:
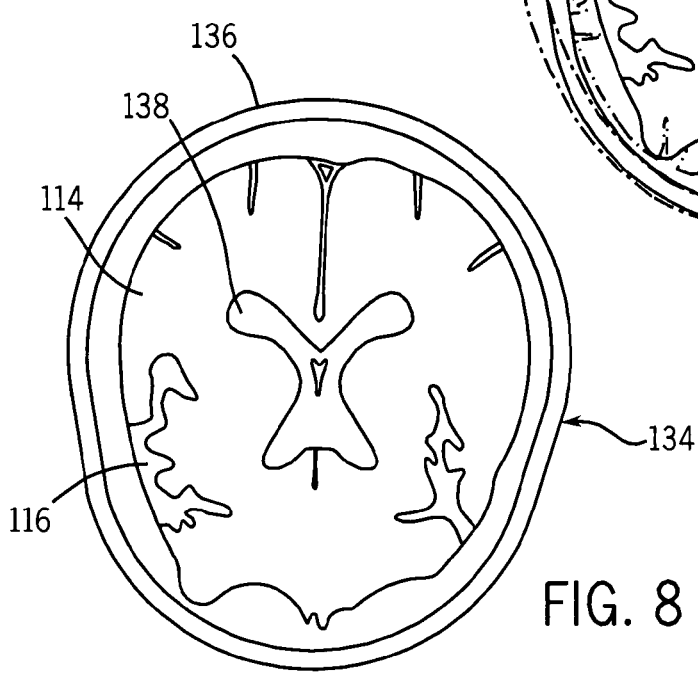
FIG. 8 is a representation of the portion of the medical image slice of FIG. 4 that is stored in long-term storage, in accordance with an exemplary embodiment of the present invention.

Referring generally to FIG. 8, a brain image slice produced from the compressed medical image data is presented, and referenced generally by reference numeral 134. The white matter 114 and gray matter 116 are produced with the same resolution as in the original medical image data obtained from the CT imaging system 20. However, the regions of the brain image slice 134 corresponding to the skull 136 are reproduced with a lesser resolution. In addition, the region 138 of the brain image slice 134 that corresponds to the cerebrospinal fluid is not reproduced. Instead, that portion of the brain image slice is blank. As a result, less data storage space was required to store the image than if all of the regions of the image had been stored at full resolution. However, those regions of the image that are the most relevant for viewing for the clinical purpose intended are presented in full resolution.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A computer-implemented method for processing image data, comprising:
    accessing image data obtained by an imaging system;
    selecting an anatomical atlas from among a plurality of anatomical atlases based on a clinical purpose for obtaining the image data;
    accessing the anatomical atlas labeled with image data compression information;
    aligning the anatomical atlas with the image data; and
    compressing the image data based on the image data compression information.

2. The computer-implemented method for processing image data as recited in claim 1, wherein a first portion of the image data is compressed with lossless compression based on the image data compression information.

3. The computer-implemented method for processing image data as recited in claim 2, wherein a second portion of the image data is compressed with lossy compression based on the image data compression information.

4. The computer-implemented method for processing image data as recited in claim 3, wherein a third portion of the image data is discarded based on the image data compression information.

5. The computer-implemented method for processing image data as recited in claim 2, wherein a second portion of the image data is discarded based on the image data compression information.

6. The computer-implemented method for processing image data as recited in claim 1, comprising:
    transferring the image data compression information from the anatomical atlas to the image data.

7. The computer-implemented method for processing image data as recited in claim 1, comprising:
    storing compressed image data in long-term storage.

8. The computer-implemented method for processing image data as recited in claim 1, wherein the image data compression information comprises a plurality of compression quality factors, each compression quality factor corresponding to a region in the anatomical atlas and its relevance to other regions in the anatomical atlas.

9. The computer-implemented method for processing image data as recited in claim 1, wherein the anatomical atlas comprises image data of at least three dimensions of image data.

10. The computer-implemented method for processing image data as recited in claim 1, wherein the anatomical atlas comprises regions labeled with image data compression information that conform substantially to specific anatomical features within the image data.

11. A computer-implemented method for storing image data, comprising:
    accessing image data obtained by an imaging system;
    accessing an anatomical atlas labeled with image data compression information;
    identifying and associating anatomical features within the image data with corresponding anatomical features within the anatomical atlas;
    compressing a first portion of the image data with lossless compression and a second portion of the image data with lossy compression based on the image data compression information; and
    discarding a third portion of the image data to keep the third portion of the image data from being stored in long-term storage based on the image data compression information, wherein the third portion of the image data comprises uncompressed image data.

12. The computer-implemented method for storing image data as recited in claim 11, comprising:
    transferring the image data compression information from the anatomical atlas to the image data.

13. The computer-implemented method for storing image data as recited in claim 11, comprising:
    aligning the anatomical atlas with the image data.

14. The computer-implemented method for storing image data as recited in claim 13, wherein aligning the anatomical atlas with the image data comprises deforming the anatomical atlas to bring the atlas into alignment with the image data.

15. The computer-implemented method for storing image data as recited in claim 11, wherein the image data compression information comprises a plurality of compression quality factors, each compression quality factor corresponding to a region in the anatomical atlas and its relative relevance to other regions in the anatomical atlas.

16. The computer-implemented method for processing image data as recited in claim 11, comprising:
    storing compressed image data in long-term storage.

17. A computer-implemented method for storing image data, comprising:
    accessing image data obtained by an imaging system;
    accessing an anatomical atlas labeled with image data compression information;
    compressing a first portion of the image data based on the image data compression information; and
    discarding a second portion of the image data to keep the second portion of the image data from being stored in long-term storage based on the image data compression information, wherein the second portion of the image data comprises uncompressed image data.

18. The computer-implemented method for storing image data as recited in claim 17, wherein compressing a first portion of the image data comprises compressing the first portion of the image data with lossless compression based on the image data compression information.

19. The computer-implemented method for storing image data as recited in claim 18, comprising:
    compressing a third portion of the image data based on the image data compression information.

20. The computer-implemented method for storing image data as recited in claim 17, comprising:
  transferring the image data compression information from the anatomical atlas to the image data.

21. The computer-implemented method for processing image data as recited in claim 17, comprising:
  storing compressed image data in long-term storage.

22. The computer-implemented method for processing image data as recited in claim 17, wherein the image data compression information comprises a plurality of compression quality factors, each compression quality factor corresponding to a region in the anatomical atlas and its relative relevance to other regions in the anatomical atlas.

23. The computer-implemented method for processing image data as recited in claim 17, comprising:
  selecting the anatomical atlas from among a plurality of anatomical atlases based on a clinical purpose for obtaining the image data.

24. The computer-implemented method for processing image data as recited in claim 17, comprising:
  aligning the anatomical atlas with the image data.

25. A system for processing image data, comprising:
  means for accessing image data obtained by an imaging system;
  means for selecting an anatomical atlas from among a plurality of anatomical atlases based on a clinical purpose for obtaining the image data;
  means for accessing the anatomical atlas labeled with image data compression information;
  means for aligning the anatomical atlas with the image data; and
  means for compressing the image data based on the image data compression information.

26. A system for storing image data, comprising:
  means for accessing image data obtained by an imaging system;
  means for accessing an anatomical atlas labeled with image data compression information;
  means for identifying and associating anatomical features within the image data with corresponding anatomical features within the anatomical atlas;
  means for compressing a first portion of the image data with lossless compression and a second portion of the image data with lossy compression based on the image data compression information; and
  means for discarding a third portion of the image data to keep the third portion of the image data from being stored in long-term storage based on the image data compression information, wherein the third portion of the image data comprises uncompressed image data.

27. A system for storing image data, comprising:
  means for accessing image data obtained by an imaging system;
  means for accessing an anatomical atlas labeled with image data compression information;
  means for compressing a first portion of the image data based on the image data compression information; and
  means for discarding a second portion of the image data to keep the second portion of the image data from being stored in long-term storage based on the image data compression information, wherein the second portion of the image data comprises uncompressed image data.

28. A non-transitory machine-readable medium for processing medical image data, comprising:
  code operable to access image data obtained by an imaging system;
  code operable to select an anatomical atlas from among a plurality of anatomical atlases based on a clinical purpose for obtaining the image data;
  code operable to access the anatomical atlas labeled with image data compression information;
  code operable to align the anatomical atlas with the image data; and
  code operable to compress the image data based on the image data compression information.

29. A non-transitory machine-readable medium for processing medical image data, comprising:
  code operable to access image data obtained by an imaging system;
  code operable to access an anatomical atlas labeled with image data compression information;
  code operable to identify and associate anatomical features within the image data with corresponding anatomical features within the anatomical atlas;
  code operable to compress a first portion of the image data with lossless compression and a second portion of the image data with lossy compression based on the image data compression information; and
  code operable to discard a third portion of the image to keep the third portion of the image data from being stored in long-term storage based on the image data compression information, wherein the third portion of the image data comprises uncompressed image data.

30. A non-transitory machine-readable medium for processing medical image data, comprising:
  code operable to access image data obtained by an imaging system;
  code operable to access an anatomical atlas labeled with image data compression information;
  code operable to compress a first portion of the image data based on the image data compression information; and
  code operable to discard a second portion of the image data to keep the second portion of the image data from being stored in long-term storage based on the image data compression information, wherein the second portion of the image data comprises uncompressed image data.

* * * * *